United States Patent [19]
Hooker

[11] 3,933,433
[45] Jan. 20, 1976

[54] METHOD AND APPARATUS FOR GAS DETECTION

[75] Inventor: Robert R. Hooker, Ypsilanti, Mich.

[73] Assignee: Dynamation Enterprises, Inc., Ann Arbor, Mich.

[22] Filed: Dec. 18, 1974

[21] Appl. No.: 534,072

[52] U.S. Cl............. 23/232 E; 23/254 E; 23/255 E; 340/237 R
[51] Int. Cl.[2]...................................... G01N 27/16
[58] Field of Search........... 23/232 E, 254 E, 255 E; 340/237 R

[56] References Cited
UNITED STATES PATENTS

| | | | |
|---|---|---|---|
| 1,791,912 | 2/1931 | Story | 23/255 E |
| 1,979,976 | 11/1934 | Marshall | 23/255 E |
| 2,857,251 | 10/1958 | Krogh | 23/255 E X |
| 2,904,406 | 9/1959 | Moore | 23/232 E |
| 3,418,914 | 12/1968 | Finkin | 340/237 R X |
| 3,482,233 | 12/1969 | OGG | 340/237 R |
| 3,603,954 | 9/1971 | Takeuchi | 23/254 E X |
| 3,865,550 | 2/1975 | Bott et al. | 23/232 E |

Primary Examiner—Robert W. Reese
Attorney, Agent, or Firm—Cullen, Settle, Sloman & Cantor

[57] ABSTRACT

A method of gas detection and differentiation between various noxious gases including exposing a semi-conductor catalytic sensor in the atmosphere to be evaluated, sequentially providing first and second voltage level inputs to the sensor, and determining the relative change in the output of the sensor as said input voltage is changed from the first level to a second level. A reduction in the output of the sensor in response to the increase in input voltage corresponds to the presence of carbon monoxide and the absence of hydrocarbons in the atmosphere being evaluated. An increase in the sensor output in response to an increase in the input voltage indicates the presence of hydrocarbons in the atmosphere being evaluated.

A method of calibrating the semi-conductor catalytic gas sensor including purging the sensor of any gas by applying a first input voltage to heat the sensor and oxidize any noxious gases collected thereon, then applying a second input voltage to the sensor in an uncontaminated atmosphere to heat the sensor to a second lower temperature, and then adjusting an indicator to a predetermined value.

8 Claims, 6 Drawing Figures

U.S. Patent  Jan. 20, 1976  Sheet 1 of 2  3,933,433
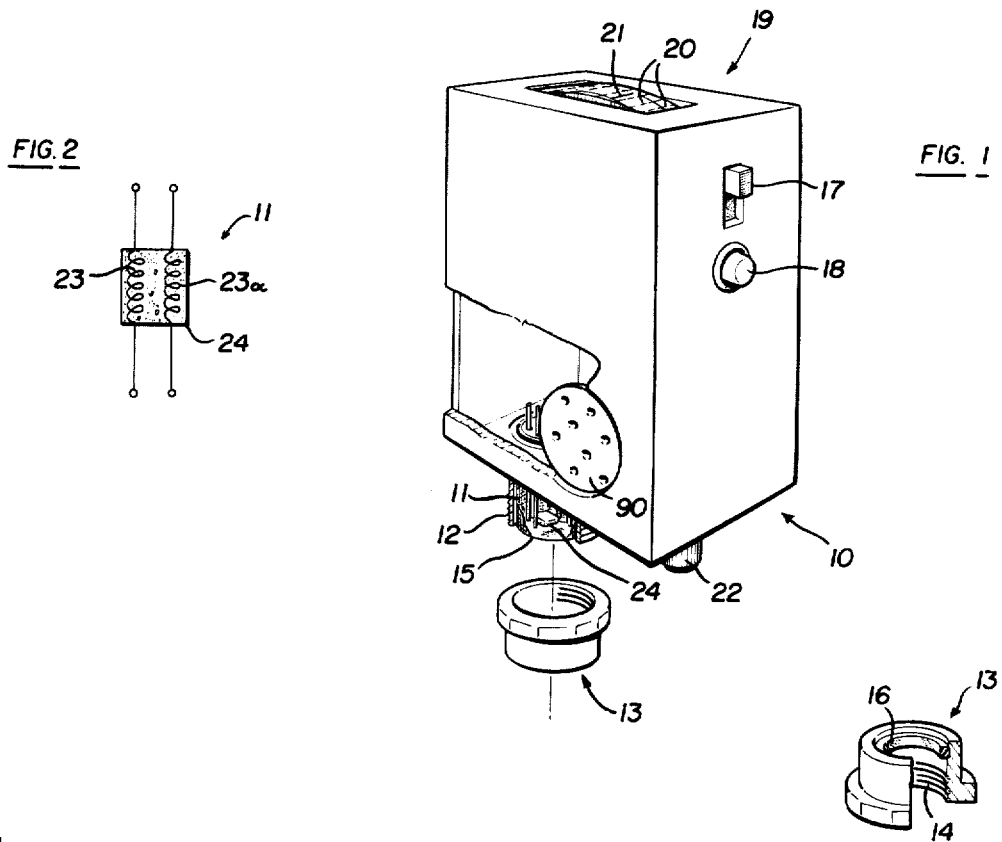
FIG. 2
FIG. 1
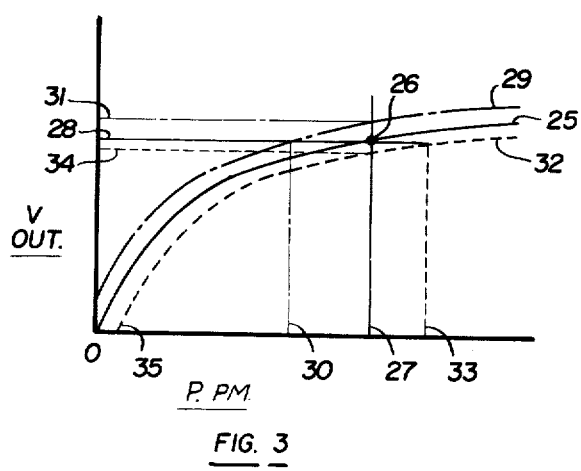
FIG. 3
FIG. 4
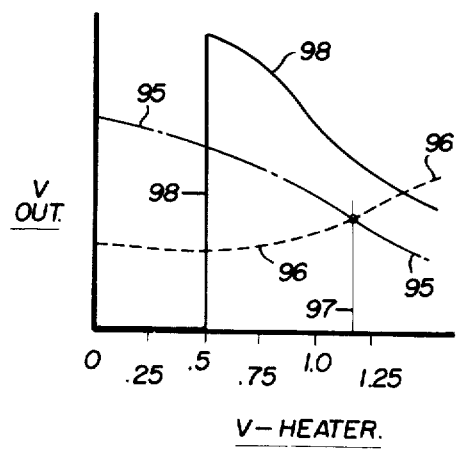
FIG. 6

METHOD AND APPARATUS FOR GAS DETECTION

The apparatus of the present invention includes a semi-conductor catalytic sensor, a voltage regulator circuit for providing discrete levels of input voltage to the sensor, and an indicator circuit response to the output of the sensor. The indicator circuit includes an audio alarm which is triggered when the gas toxicity reaches a predetermined level.

The gas sensor includes a calibration feature to compensate for sensor variations between usages and a switch for selecting the appropriate input voltage levels to the sensors for first purging the sensor, and then for calibration as well as for sensing gases and differentiating between gases. A moisturizing collar is also provided for operation of the sensor at the desired relative humidity level.

BACKGROUND OF THE INVENTION

This invention relates generally to a method and apparatus for detecting the presence of harmful gases and, more specifically, to an improved gas detection apparatus which can differentiate between various noxious gases.

While gas measuring and detection instruments are well-known, recent government regulation has created a need for more precise, more reliable and faster responding instruments. The EPA (Environmental Protection Agency) has the overall responsibility for assuring that the atmosphere which we all breathe is relatively free of dangerous contaminants. In addition, the OHSA (Occupational Health and Safety Act) has set standards for the air which workers breathe to insure that the air is free from toxic, noxious and hazardous substances which might endanger the worker's health or safety.

For example, with respect to carbon monoxide, under OHSA the government has established a maximum contaminant level of 50 ppm (parts per million) average, over an eight hour time interval, and a 200 ppm maximum at any one time.

Various problems have been encountered with the prior gas detection and monitoring instruments. For example, as might be expected, the industrial needs include low cost instrumentation which is portable, accurate and reliable. Furthermore, industry needs instrumentation which can differentiate among various gases because of the different critical contaminant levels of different gases.

In addition, rather than only intermittent testing, a detector which operates continuously is important in industry so that a worker may carry the detector with him through a plant or wear it on his person to sense the presence of a potentially noxious gas and to provide an alarm. While permanently mounted fixed monitors may be placed in high-risk areas, the high-risk areas must be first identified with the use of continuously operating portable instruments. It is not practical to go through a plant initially with an instrument which must be repeatedly triggered to evaluate the atmosphere. Pockets of noxious gases may be missed easily. Thus, continuous operation is an important industrial prerequisite.

Obviously, the gas detection instruments must be of low cost since they do not add to the profitability of the product manufactured. Of course, accuracy and reliability is also of critical importance because of the potential financial penalties which may be assessed under the OHSA for non-compliance.

Furthermore, a significant factor in compliance with OHSA standards is fast response, i.e., the ability of the gas detector to respond virtually immediately to indicate both the presence and amount of toxic gases. As a practical matter, a gas detection system which requires several hours to provide an indication of toxicity level is of dubious value to the worker who has been breathing toxic fumes for those several hours.

In addition, depending on the particular environment, the gas detection instrument must be selective, i.e., the instrument should respond to the presence of a gas such as carbon monoxide and it should be able to differentiate between that gas and other gases such as hydrocarbons.

However, all types of gas detection devices prior to the present invention had at least one drawback. The chemical types of sensor, including the colorimetric systems, are relatively slow and non-continuous. A sample of gas is introduced through a powdered reagent into a tube and a visible color change or stain occurs. The length of the stain must be physically measured to determine the concentration or contamination level. Thus, systems relying on chemical reactions are slow, non-continuous and costly. Furthermore, the tubes, once stained, are not reusable.

The optical systems rely on the infrared absorption spectra of the gas. These systems are not portable and are too expensive to install at various locations in a plant. In the absence of portability, continuous sampling and prompt indications of toxicity levels, optical systems are not feasible.

A third type of system utilized to detect the presence of toxic gas is gas chromatography in which a sample of gas is injected into an absorption column and the reaction is timed and observed. Thus, a slow response and non-continuous sampling are obvious drawbacks of gas chromatography systems.

A fourth prior art system is electrochemical gas detection wherein an oxidation-reduction reaction takes place in a fuel cell with the gas being sampled serving as one electrolyte. The fuel cell generates a current proportional to the electrolyte concentration and this type of system requires a pump and filter, reference electrodes, oxidation and reduction electrodes, feedback voltage circuitry and readout circuitry as well as the secondary electrolyte (typically sulphuric acid). This type of system, however, cannot selectively identify carbon monoxide, is quite complex and not generally satisfactory.

Because of the OHSA requirement of an average contaminant level over an eight-hour period, a portable system must operate without interruption for recharging for at least an eight-hour period. The system must operate continuously since the presence of toxic gases often occurs as a small "air pocket" and intermittent sampling of the air could result in the instrument operator missing the presence of an air pocket.

BRIEF DESCRIPTION OF THE INVENTION

To provide a low cost portable, continuously operable gas detection unit, a catalytic sensor is required. There are two types of catalytic sensors commonly in use, the thermal type which measures the temperature change of the catalytic material and the semi-conductor catalytic sensor.

One typical thermal type of catalytic sensor is hopcalite, which operates by carbon monoxide being oxidized by the hopcalite. This reaction requires dry air; the reaction occurs by drawing dry air through the detector cell, and the oxidation rate is based on the carbon monoxide concentration level which results in the relative temperature change of the hopcalite. Thermistors measure the temperature rise of the hopcalite material and the change in temperature is registered on a meter. This is an indirect measurement of carbon monoxide since it is a temperature measurement and thus is not preferred.

The semi-conductor type of catalytic sensor is composed of largely tin oxide material in which the impedance directly changes when the catalytic tin oxide material in which the impedance directly changes when the catalytic reaction takes place. The semi-conductor material is heated to approximately 300°F and when carbon monoxide contacts the metal oxides, a catalytic reaction takes place. This reaction changes the semi-conductor's impedance, which may be measured and read directly on a meter. This catalytic reaction will always take place given the proper heated metal oxides, but the reaction must occur the same each time so that a repeatable measurement can be made.

It has now been determined that semi-conductor catalytic sensors are sensitive to humidity changes, sensor heater voltage or heater temperature, and to sensor variations between usage. At zero humidity, the sensor barely reacts to 50 ppm of gas. At 25% humidity, a true 50 ppm reading would be 20 ppm, at 50% humidity — 35 ppm, 75% humidity — 45 ppm. It is apparent that changes in humidity above 50% creates less error than when the humidity is less than 50%.

Small heater variances effect the output reading of the instrument. The heater voltage will change from battery discharge on portable units. Typically, only 0.05 of a volt variance gives a 20 ppm difference at 50 ppm true concentration. It has been found that at a true 50 ppm the unit could read 35 to 75 ppm if not zeroed after a period of inactivity.

The device of the present invention has been developed to compensate for those variables. The humidity compensation is accomplished by a moisturizing ring that surrounds the sensor on the portable unit. This ring is moistened before testing especially when the humidity is below 50%.

A circuit has been incorporated in the portable unit that gives the sensor a constant heater voltage and temperature to eliminate variances from the DC battery supply.

The present invention has an adjustment control to eliminate the variations from a non-zeroed instrument. For better accuracy, the zero adjustment is done at 50 ppm instead of zero and is named the Set Point Adjustment. This set point adjustment does more than zero the meter, it also compensates for sensor composition changes, drift and other variables which permits the unit to make repeatable readings.

The sensor of the present invention also differentiates between carbon monoxide and other noxious gases. This is based on my discovery that the sensitivity of the semi-conductor catalytic converter may be varied by changing the converter input voltage, and further that such sensitivity variations provide different relative impedance changes depending upon the particular noxious gases being oxidized.

OBJECTS OF THE INVENTION

It is an object of the present invention to provide an improved direct reading apparatus for sensing the presence of noxious gases and for differentiating between carbon monoxide and other noxious gases including hydrocarbons, the apparatus including a semi-conductor catalytic gas sensor, a voltage regulator for providing input voltage at first and second levels to the sensor, and an output means including a scale and an indicator for indicating the output of the sensor at each input power level and for further indicating the relative change in the output of the sensor as the input power is changed from the first level to the second level.

It is another object of the present invention to provide a gas detector having a calibration feature to compensate for gas sensor variations between usages, including a switch for selecting the appropriate voltage input level to the sensor for first purging the sensor of accumulated noxious gases and then providing a second voltage input to the sensor for calibration purposes.

It is yet another object of the present invention to provide an improved apparatus for detecting the presence of noxious gases and including a semi-conductor catalytic sensor, a constant voltage heater source for said sensor and means for insuring the humidity level of the noxious gas exposed to the sensor.

It is yet another object of the present invention to provide a method of calibrating a semi-conductor catalytic gas sensor, an input voltage regulator and an output means including a scale and an indicator, said calibrating method including purging the sensor of any accumulated gas by applying a first input voltage to the sensor to heat the sensor and to oxidize any noxious gases accumulated thereon until the output means stabilizes at a constant output level, then applying a second input voltage to said sensor in an uncontaminated atmosphere to heat the sensor to a second level lower than the first level, and then adjusting the output indicator to a predetermined position on said scale.

Still another object of the present invention is the provision of an improved method for detecting the presence of noxious gases and for differentiating among noxious gases with a semi-conductor catalytic converter including providing first and second voltage input levels to said converter, directly sensing the change in impedance of said converter at said two voltage input levels, and determining the relative change in said impedance as said voltage is changed from said first level to said second level.

IN THE DRAWINGS

The various objects of the present invention, together with other objects and advantages which may be attained by its use, will become more apparent upon reading the following detailed description taken in conjunction with the drawings.

In the drawings, wherein the reference numerals identify corrsponding parts:

FIG. 1 is a partly broken away pictorial illustration of the gas detector of the present invention;

FIG. 2 is an enlarged sectional illustration of the sensor of the present invention;

FIG. 3 is a graph illustrating the calibration feature of the present invention;

FIG. 4 is an illustration of the moisturizing collar of the present invention;

FIG. 6 is a graph illustrating the change in sensitivity of the catalytic converter as utilized for differentiating among noxious gases.

AS SHOWN IN THE DRAWINGS

Figure 5:
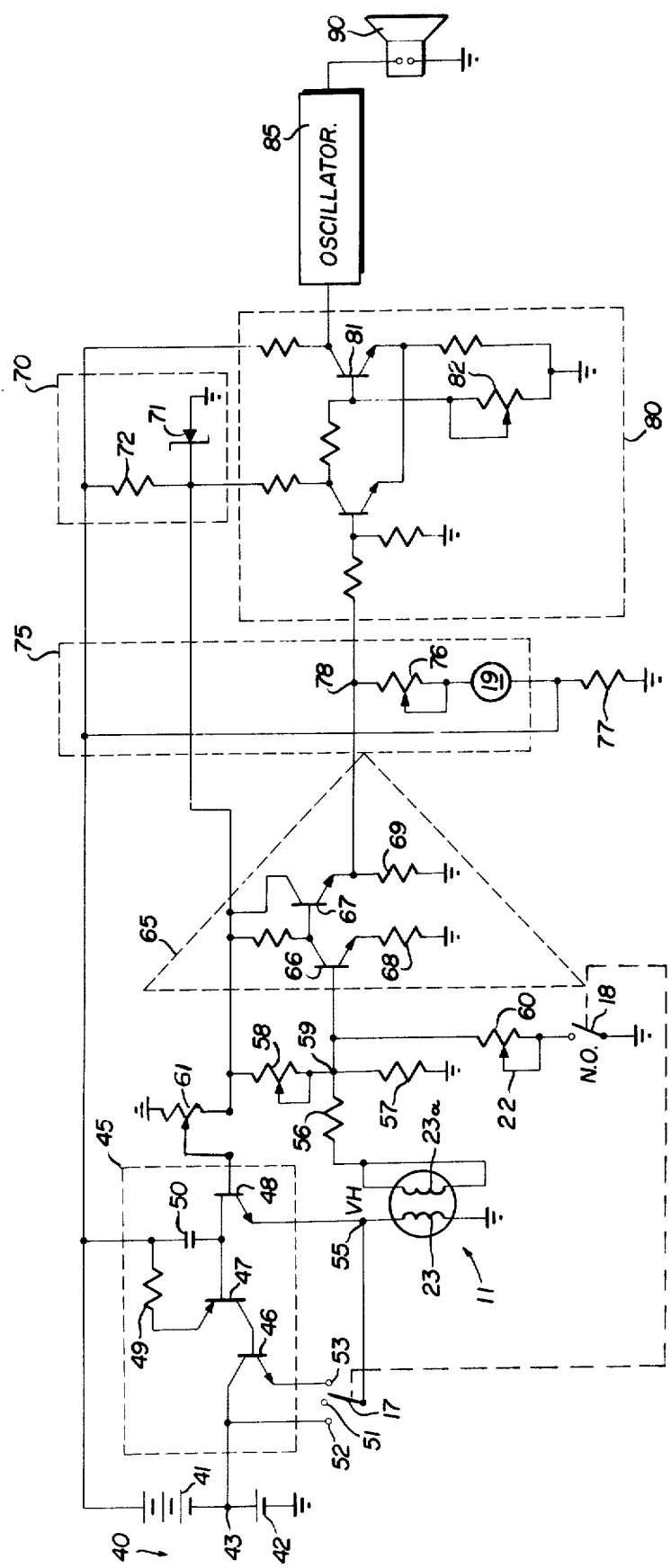
FIG. 5 is a circuit diagram showing electronic circuitry of the present invention.

For a more complete understanding of the operation of the gas detection apparatus and the method of using the same, a preliminary explanation of the principles of the gas sensor operation is provided. The sensor is a semi-conductor catalytic converter composed of metal oxides, largely tin oxide material. The metal oxides react with carbon monoxide to catalyze CO to $CO_2$. Hydrocarbons are catalyzed to $CO_2$ plus water. The catalytic reaction changes the electrical impedance characteristics of the semi-conductor which changes can be directly measured on a meter.

More specifically, the catalytic converter includes a pair of balanced electrical coils imbedded in the metal oxides. One coil is heated by the instrumentation. As the metal oxides react with the toxic gases, the oxide impedance changes and the change in impedance is measured from the second coil to ground to drive an indicating device such as a meter.

Referring more particularly to the drawings, the gas detection apparatus 10 includes a sensor 11 mounted interiorly of a hollow externally threaded shaft 12 which provides an air flow passage between the sensor and the air being sampled. Threaded onto and surrounding the shaft 12 is a moisturizing collar 13 having internal threads 14.

The sensor 11 is mounted in a housing which is open on one side, by virtue of a a 100 mesh stainless steel gauze lattice 15. This gauze lattice is shown as being at the bottom of the sensor in FIG. 1. The toxic gas flows through the shaft and the lattice by normal diffusion and ambient convection. The heat of the sensor including the heat generated by oxidation causes additional convection currents to be established and the oxidized gas flows outwardly through the gauze lattice and exits through the shaft 12. Thus, the shaft 12 provides both a support for the collar 13 and an inlet/outlet air flow passage.

It has been discovered that the calibration of the sensor 11 of the present invention is not reliable if operated in an atmosphere having less than 50% relative humidity. To prevent a loss in reliability, the moisturizing collar 13 is provided with a wick or spongy material 16 which may be kept moistened on a regular basis. Since the moisturizing collar surrounds the air flow passage (shaft 12) there is assurance that the atmosphere being sensed is at the minimum relative humidity necessary for reliable operation.

The detector 10 includes a first switch 17 which has three positions as will be explained in greater detail and a normally open second switch 18. Visual output means 19 are provided including a logarithmic scale 20 and an indicator 21. A knurled adjustment knob 22 is provided to manually position the indicator 21 on the scale 20.

The sensor 11 is a catalytic converter including a pair of balanced electrical coils 23 and 23a imbedded in a catalyst or metal oxide bed 24. The first coil 23 is utilized as a heater coil and the opposite coil 23a functions as an electrode. The impedance of the bead is measured and changes in this impedance, indicative of catalytic reactions and hence the concentration of contaminants, are reflected as impedance changes measured from the output coil 23a to ground.

An inherent problem with catalytic converters of this type is their logarithmic response at low contamination levels. With specific reference to FIG. 3, this is illustrated by comparison to the solid or "normal" curve 25. Thus, as the concentration increases initially from O there is a much greater change in voltage output (assuming the same heater voltage or voltage input), and as the concentration continues to increase the magnitude of the voltage changes decreases to an almost linear portion of the curve 25.

Thus, it must be appreciated that a significant error may occur in reading low concentrations of contaminants. The smallest change in contaminant concentration at low contaminant levels will cause a large voltage variation. Hence, catalytic converter operations and calibrations at low concentrations are inaccurate without the addition of complex, expensive additional circuitry.

To compensate for these problems, the detector of the present invention is calibrated at a linear portion of the normal curve 25. Specifically, calibration should be accomplished at a "mid-point" on the logarithmic scale 20 such as shown at the point 26 on the graph of FIG. 3. A point 26 is shown on normal curve 25 corresponding to a contaminant concentration level indicated at 27 and a voltage output level indicated at 28.

To explain the problem of low concentration converter operation and calibration, consider the dashed response curve 29. This curve is slightly higher than the normal curve 25. The voltage output indicated at 28 from normal curve 25 would reflect a much lower contaminant concentration as shown at 30 if the sensor was erroneously calibrated and operated on curve 29. Since the scale is logarithmic, concentration 30 could easily be a significant variation from concentration 27. Similarly, at the same concentration as 27, the voltage output would be higher as shown as level 31 if the sensor was operated on curve 29.

On the lower side of normal curve 25 as shown by the dotted curve 32 also indicating erroneous calibration, the initial voltage output shown at 28 would result in a high misreading as contaminant level 33 whereas the proper contaminant level shown at 27 would yield an erroneous lower voltage output reading as shown at voltage level 34.

Considering this latter situation, if the converter was calibrated to zero but the actual concentration was 1 ppm (erroneously thought to be 0 ppm), as shown at point 35 on the graph, then the calibrated curve for the particular catalytic converter would be the dotted curve 32 instead of the true curve 25. Thus, upon reaching a voltage level at 28 which should reflect the concentration level 27 (assume this to be the critical concentration), the actual concentration which yields this voltage is the higher concentration shown as level 33. Since this exceeds the critical concentration, then we have a situation where an excessive concentration has been necessary to indicate a critical concentration level.

To compensate for and eliminate this problem, I have discovered that the catalytic converter of the present invention should always be calibrated somewhere around the middle of the scale 20. Specifically, since the indicia on the scale can always be changed, calibration should take place on a linear portion of the logarithmic response curve of the converter.

Having thus explained the calibration principles and the principles of operation of the converter, reference should be had to the circuit diagram for a more complete understanding of the present invention. The power may be supplied in one of two fashions. The power supply 40 can be two batteries 41 and 42 of 4.8 volts and 1.2 volts respectively, connected together at center terminal 43. Alternatively, 110 volt line voltage can be used with conventional circuitry to obtain the equivalent voltages.

The circuit includes a voltage regulator portion shown within the block 45. The voltage regulator includes a first transistor 46, a second transistor 47 and a third transistor 48. The collector of the first transistor is connected to the common point 43 between the two batteries. The base of the first transistor is connected to the collector of the second transistor 47 and the base of the second transistor 47 is connected to the collector of the third transistor 48. In the circuit from the emitter of transistor 47 to the collector of transistor 48 are a series resistor 49 and capacitor 50 with the common connection between the resistor and capacitor connected to the high voltage side of the power supply 40.

Switch 17, illustrated in this figure as well as in FIG. 1, is a three position switch corresponding to the three terminals 51, 52 and 53. Position 51 is the OFF position. When the switch is in position 52 there is a direct path from the positive side of the 1.2 volt battery to the heater coil 23 of the catalytic converter 11. Thus at the terminal $V_h$ the 1.2 volt is the applied heater voltage.

When the switch 17 is in position 3, i.e., terminal 53, the heater voltage is a lower value depending upon the overall resistance of the voltage regulator circuit 45. In a preferred embodiment this would be 0.75 volts as will be explained later.

As explained previously, the heater voltage or voltage applied to the input side of the catalytic converter is that voltage between terminal 55 and ground. The output of the catalytic converter is a variable impedance depending upon the concentration of contaminants. The output of the catalytic converter is coupled through a series resistor 56 then to a voltage divider network including a resistor 57 and a potentiometer or variable resistor 58 all three of which are connected together at a common point 59.

Also connected at this terminal 59 is a second potentiometer 60 connected to the normally open switch 18 previously discussed. The opposite end of the normally open switch 18 is grounded.

The output from the catalytic converter and the voltage divider network is coupled to a DC amplifier shown in the block 65, the DC amplifier including transistor 66 and 67 each having their emitters grounded through a resistor 68, 69 respectively as is conventional. The voltage divider input is coupled to the base of the first transistor 66 and the collector of the first transistor is connected directly to the base of the second transistor. Suitable conventional biasing voltage is provided to each collector.

In addition to the voltage regulator 45 it is necessary to provide a voltage reference level for biasing the various transistors. To this end, as is known, there is provided a voltage reference circuit 70 including a Zener diode 71 and a series resistor 72. One side of the Zener is grounded and the other side is connected through resistor 72 to the power supply 40.

The output of the DC amplifier 65 is connected to a meter drive circuit 75. The meter drive circuit operates so that the meter can be a conventional volt meter measuring the voltage drop across a resistor. To accomplish this, the meter drive circuit 75 takes its output from DC amplifier 65 and includes a first potentiometer 76 connected to one side of the meter 19 having a scale 20 and indicator 21 as illustrated in FIG. 1. The other side of the meter is connected through a resistor 77 to ground so that the meter is floating as is known for zero suppression at the lower end of the logarithmic scale. The junction between the potentiometer 76 and the output from the DC amplifier 65 is shown as a terminal 78 and this terminal is utilized if it is desired to record the output on a graph or other recording device.

The output of the DC amplifier also serves as the input to a Schmitt trigger circuit 80. The Schmitt trigger circuit 80 is conventional and hence will not be described in greater detail except to point out one particular feature with respect to the second transistor 81. Transistor 81 has a potentiometer 82 coupled between its base and ground for adjustment of the trigger point. The output taken from the collector of transistor 81 drives a conventional threshold oscillator circuit 85 which is connected to an audio alarm indicated as a speaker 90.

Having thus explained the circuit, the method of operating the gas detection apparatus will now be explained.

Each time that the gas detector is to be turned on, the first step is to purge the catalytic converter 11 of any accumulated contaminants. This is done by moving switch 17 to the first position corresponding to terminal 52. The 1.2 volts is supplied to heat the converter raising the converter temperature to the range of 400°F. This serves to accelerate oxidation of any contaminants on the converter.

After the indicator reading has stabilized the purging is completed. The stabilization is shown by a relatively constant output of the indicator 21 of the meter 19.

The next step is to move switch 17 to its next position corresponding to terminal 53. The heater voltage reflected at terminal 55 drops to a preselected value depending upon the gas to be detected. If it is desired to detect carbon monoxide, then the heater voltage level would be 0.75 volts. If it is desired to detect vinyl chloride then a heater voltage of 1.0 volts would be applied. Obviously, this can be adjusted by virtue of the circuit including resistor 61. With the switch 17 in this third position at terminal 53 the temperature of the converter will be about 300°F.

The next step is to calibrate the apparatus in a noncontaminated atmosphere. The need for calibration at a linear portion of the response curve has been explained. To accomplish this with circuitry, there is provided a calibration circuit which provides the equivalent voltage output of the converter at a point in the linear portion of the catalytic converter response curve.

To simplify this explanation, when the gas detection apparatus is set up at the factory to detect carbon monoxide, it has been found that the contaminant level of 50 ppm is on the linear portion of the response curve and substantially at the middle of the scale. Thus, we use the 50 ppm midpoint as a calibration point. The circuitry including the resistor 57 and potentiometer 60 are selected to provide an approximate reading equivalent to the voltage output of the catalytic converter in the presence of a comtamination level of 50 ppm. Thus, to calibrate, switch 18 is closed and the meter 19 is observed to determine where the indicator 21 will stabilize. If the indicator stabilizes at a point other than 50 ppm, the adjusting knob 22 is turned until the meter is calibrated at 50 ppm. Thus, adjusting knob 22 is the wiper of potentiometer 60. Once the calibration step is complete, the switch 18 is returned to its normally open position.

It should be noted that closing switch 18 simulates an impedance change at terminal 59 identical to the impedance change of the converter. At this terminal there occurs a direct reading of the converter impedance of output coil 23a. Thus, while the voltage is amplified to drive the meter, there is still direct reading of impedance, as contrasted with the thermal type converters which measure a change in temperature.

As shown by the dashed line in FIG. 5, switches 17 and 18 are tied together so that closing switch 18 for calibration purposes also moves switch 17 to position 3 (terminal 53). Thus, calibration occurs at a heater voltage of 0.75 volts which conforms to the normal operating heater voltage.

At this point, a word should be said about the need for calibration in a non-contaminated atmosphere. In a non-contaminated atmosphere, the output of the catalytic converter should be at the quiescent level. Thus, there is no additive effect between the output of the converter and the output of the test circuit when the normally open switch 18 is closed. Thus, it may be seen that the normally open switch 18, when closed, provides a bias to the entire system equivalent to a contamination level of 50 ppm.

Since the initial part of the logarithmic response is so steep that low contamination levels cannot be accurately read, it must be appreciated that by keeping switch 18 closed and thus biasing the system to 50 ppm, levels of contamination of 51, 52 or 53 ppm with switch 18 closed, are substantially equivalent to actual contamination levels of 1, 2 or 3 ppm respectively. Thus, indications of low contaminant levels can be obtained in this fashion.

As an alternative method of calibration with switch 17 in position 3 and switch 18 open, the sensor may be exposed to a known carbon monoxide level using a conventional calibration chamber having its own moisturizing collar and threaded onto shaft 12. Rotation of knob 22 adjusts the indicator to the known concentration of contaminants in the chamber.

Once calibration has been completed and switch 18 opened, the meter or output means 19 is observed to indicate the concentration level. The Schmitt trigger is calibrated to turn on the oscillator and the alarm at a predetermined concentration level. In the case of carbon monoxide, this would be set for 200 ppm which is the OHSA maximum one time contaminant level.

To provide this adjustment, the potentiometer 82 is provided to the base of the second transistor 81 in the Schmitt trigger circuitry. This is an internal adjustment in the apparatus so that the audio alarm can be sounded at any desired contaminant level. It must be appreciated that "contaminant level" is reflected as "voltage output" regardless of what the actual scale numerals are on the scale 20. This, however, is true of any meter.

The feature of distinguishing among hazardous gases will now be explained. I have discovered that with the sensor of the present invention, the output is dependent not only upon the relative humidity but also upon the heater voltage at terminal 55. To compensate for problems of relative humidity the moisturizing collar 13 has been provided as previously explained.

Consider the situation where the gas detector is being operated with switch 17 in position 53, i.e., 0.75 volts as the heater voltage. I have discovered that by switching to a higher heater voltage of 1.2 volts at terminal 52, if only carbon monoxide is present, the voltage output of the catalytic converter and the meter reading drop. If other toxic gases such as hydrocarbons are present then upon increasing the heater voltage, the sensor voltage output increases and the meter reading increases.

FIG. 6 is a graph of converter sensitivity as a function of heater voltage (the voltage across coil 23) for different gases. Curve 95 is a typical response curve for carbon monoxide. As heater voltage is increased the sensitivity of the sensor decreases and hence the output (change in impedance) is reduced at a given concentration. At that same concentration, a different gas such as methane has a response curve 96 showing an increase in sensitivity at increased heater voltages. The two curves intersect at 97.

Thus, by increasing heater voltage if only carbon monoxide is present, the output voltage drops (curve 95) but if a hydrocarbon such as methane is present the output voltage increases (curve 96). If both gases are present the output voltage is initially higher and increases although slightly less than methane alone being present, because the cumulative effects of the two gases results in an increased output.

Curve 98 is a typical response curve for another toxic gas, isobutane, illustrating the step or threshold which occurs at a 0.50 heater voltage. Thus, below the threshold heater voltage the converter cannot detect this type of gas. Knowledge of the converter response curve is important to insure that all purging, detecting and differentiating of gases, i.e., all converter operations, occur above the threshold heater voltage.

Hence, based upon this discovery, it is possible to not only sense the toxicity level or contaminant level but to distinguish among various toxic gases. By moving switch 17 and observing either the decrease or increase in the output of the gas detector, the presence of only carbon monoxide can be determined and the presence or absence of other toxic contaminants may also be determined.

As may be appreciated, it is possible to provide an indicator circuit to accomplish this same result by utilizing a differential comparator and two indicator lights, one indicator light to show if the second input to the comparator is higher and the other indicator light to show if the second input to the comparator is lower where the two inputs to the comparator are the output from the DC amplifier 65 taken at terminal 78 before and after the switch 17 is moved.

Much of the circuitry shown in the figure can be designed to individual specifications. However, in order to provide a more complete description of the invention, the following information is provided. The catalytic converter is the model TGS solid state gas sensor manufactured by Figaro of Osaka, Japan. With respect to the voltage regulating circuit 45, resistor 49 has a resistance of 120 ohms, capacitor 50 is 1 uf, and the transistors 46, 47 and 48 are 2N 6179, 2N 4126, and 2N 3104, respectively.

In the test and biasing circuit from the output of the sensor, resistor 56 is 560 ohms, resistor 57 is 68 k ohms, variable resistor 58 is 20 k ohms and variable resistor 60 is 50 k ohms. With respect to the DC amplifier circuit 65, both transistors are 2N 3416 and the emitter bias resistors are 1,2 k ohms and 1.8 k ohms, respectively. The collector bias resistor for transistor 66 is 2.7 k ohms. Potentiometer 76 is 5 k ohms.

With respect to the reference voltage circuit 70, the Zener diode is type 1N 5229 and resistor 72 is 100 ohms. In the Schmitt trigger circuit, the input resistor is 1.2 k ohms and the grounding resistor providing a bias at the base of the first transistor is 6.8 k ohms. The two transistors are 2N 3416s and both of their emitters are biased with a 1 k ohm resistor. The variable resistor 82 utilized to adjust the audio signaling level is a 10 k ohm potentiometer. The collector of the first transistor has in its circuit a 2.2 k ohm resistor connected to the reference voltage circuit 70 and a 2.7 k ohm resistor connected to the base of the second transistor 81. The oscillator circuit is conventional for providing an alarm through a 8 ohm 0.1 watt speaker 90.

The foregoing is a complete description of the preferred embodiment of the present invention. It must be appreciated that many different circuits can be derived to provide the same functions and that many modifications and variations can be made without departing from the spirit and scope of the present invention. The invention, therefore, should be limited only by the following claims.

What is claimed is:

1. A method for continuously sensing the presence of noxious gases in the atmosphere and for differentiating between carbon monoxide and other noxious gases including hydrocarbons, including the steps of providing a semi-conductor catalytic sensor, flowing the gas to be sensed along a flow path to said sensor, moisturizing the gas in said flow path to at least 50% relative humidity, exposing said moisturized gas to said sensor for oxidation of said gas, sequentially applying input voltages at first ans second levels to said sensor, and determining the relative change in the impedance of said sensor as said input voltage is changed from said first level to said second level.

2. In the method as defined in claim 1 wherein said sensor has a decreasing sensitivity to carbon monoxide at increased input voltages and an increasing sensitivity to hydrocarbons at increased input voltages and wherein the sensitivity to both carbon monoxide and hydrocarbons are equal at a predetermined input voltage, said steps of sequentially applying input voltages further includes applying said input voltage at a first level below said predetermined voltage and applying said input voltage at a second level above said predetermined voltage.

3. A method for continuously and accurately sensing the presence of noxious gases in the atmosphere including the steps of providing a semi-conductor catalytic converter, flowing the gas to be sensed along a flow path to said converter, moisturizing the gas in said flow path to at least 50% relative humidity, exposing said moisturized gas to said converter, applying an input voltage to said converter to heat said converter and thus oxidize the gases being sensed, the impedance of said converter changing in proportion to the concentration of noxious gases, and deriving a signal indicative of said concentration of noxious gases in response to said impedance change.

4. The method of claim 3 wherein said step of mositurizing the gas in said flow path to at least 50% relative humidity comprehends the steps of providing a water-absorbent element capable of retaining moisture, wetting said element with water and interposing said wetted element in said flow path.

5. A method for detecting the presence of a first noxious gas in the atmosphere and for determining the presence of interferring noxious gases in the atmosphere including the steps of providing a semi-conductor catalytic converter having predetermined sensitivities to said first gas at first and second input voltages, said converter having a different sensitivity to interferring gases at least at one of said input voltages, flowing the gas to be sensed along a flow path to said converter, moisturizing the gas in said flow path to at least 50% relative humidity, exposing said moisturized gas to said converter, sequentially applying first and second input voltages to said converter, and determining the presence or absence of interferring gases by the relative change in impedance of said converter as said input voltage is changed from said first level to said second level as compared to the expected change in impedance based upon converter sensitivity to said first gas.

6. Apparatus for sensing the presence of noxious gases in the atmosphere and for differentiating between first and second different noxious gases including a single semi-conductor catalytic converter, means for defining a gas flow path between the atmosphere and the single semi-conductor catalytic converter, a moisturizing element interposed in said floww path for moisturizing said atmosphere to at least 50% relative humidity, a voltage regulator for supplying input voltages to said single semi-conductor catalytic converter at discrete levels, a switch means connected between said voltage regulator and said converter for selecting and coupling discrete input voltage levels to said single semi-conductor catalytic converter, and means for measuring the output of said single semi-conductor catalytic converter, said single semi-conductor catalytic converter output changing in inverse proportion to the change in input voltages if only said first noxious gas is present; said single semi-conductor catalytic converter output changing in direction proportion to the change in input voltage if at least said second noxious gas is present.

7. The apparatus as defined in claim 6 wherein said path defining means is a threaded shaft, said moisturizing element includes a collar threaded on said shaft, said collar having an internal reusable moisturizing wick.

8. The apparatus as defined in claim 6 wherein said output measuring means measures the impedance of said converter.

* * * * *